United States Patent [19]

Shami

[11] Patent Number: 5,224,964
[45] Date of Patent: Jul. 6, 1993

[54] METHOD FOR LIGHTENING AND PERMANENTLY COLORING HAIR

[76] Inventor: Farouk M. Shami, 18 Hornbill Ct., The Woodlands, Tex. 77380

[21] Appl. No.: 290,890

[22] Filed: Dec. 22, 1988

Related U.S. Application Data

[63] Continuation of Ser. No. 922,772, Oct. 27, 1986, abandoned, which is a continuation of Ser. No. 689,170, Jan. 7, 1985, abandoned.

[51] Int. Cl.$^5$ .............................. A61K 7/13
[52] U.S. Cl. ............................ 8/405; 8/428
[58] Field of Search ...................... 8/405, 428

[56] References Cited

U.S. PATENT DOCUMENTS

| | | | |
|---|---|---|---|
| 3,578,387 | 5/1971 | Zviak et al. | 8/10.1 |
| 3,811,830 | 5/1974 | De Marco | 8/405 |
| 3,898,032 | 8/1975 | Edman et al. | 8/10.2 |
| 3,912,446 | 10/1975 | Zviak et al. | 8/10.1 |
| 3,931,912 | 1/1976 | Hsiung | 222/94 |
| 4,114,632 | 9/1978 | Morganroth | 8/405 |
| 4,473,374 | 9/1984 | Bugaut et al. | 8/405 |
| 4,517,175 | 5/1985 | Iwabuchi et al. | 514/456 |
| 4,559,057 | 12/1985 | Bogaty et al. | 8/405 |

OTHER PUBLICATIONS

Sagarin. (Ed)Cosmetics Science and Technology, vol. 2, p. 295 1972.
Lady Clairol Maxi Blonde.
Loreal Super Blonde Lightener Kit.
Revlon Colorsilk Frost & Glow.
Harry's Cosmeticology, pp. 521–554. (1982).

*Primary Examiner*—Zohreh A. Fay
*Attorney, Agent, or Firm*—Arnold, White & Durkee

[57] ABSTRACT

A method and composition for lightening and imparting color to hair is disclosed which achieves a more permanent or longer lasting effect than achievable with traditional oxidation type dyes. A bleaching agent which is capable of lightening hair to a predetermined degree, and a non-oxidation type colorant which is capable of imparting a permanent color is applied to hair for a sufficient length of time and in a sufficient amount to achieve the desired result. The bleaching agent and colorant are then rinsed from the hair.

21 Claims, No Drawings

METHOD FOR LIGHTENING AND PERMANENTLY COLORING HAIR

This application is a continuation of application Ser. No. 922,772 filed Oct. 27, 1986 now abandoned which is a continuation of application Ser. No. 689,170 filed Jan. 7, 1985 now abandoned.

BACKGROUND OF THE INVENTION

The present invention relates generally to methods of coloring hair and more particularly to lightening the natural color of the hair while simultaneously imparting one or more shades which complement the lightened natural hair color.

Coloring hair as an act of adornment by men and women exists in most civilizations. It is estimated that 30–40% of the women in industrialized nations color their hair either in the home using commercially available home hair coloring products or at a salon by a professional hairdresser.

Various systems for coloring hair exist. Temporary hair colorings are those which last generally until the first shampoo. The colors employed, often referred to as fugitive colors, are typically of a higher molecular weight and are incapable of penetrating the cortex of the hair and consequently are externally deposited on the hair.

Temporary hair dyes are generally basic dyes, acid dyes, disperse dyes, pigments or metallized dyes, belonging to various chemical classes including azo, anthraquinone, triphenylmethane, phenazinic, xanthenic, and benzoquinoneimine.

Semi-permanent hair coloring is resistant to several shampooings. The colors employed are typically direct dyes of low molecular weight and capable of penetrating the cortex of the hair. Semi-permanent hair colorings belong generally to the chemical classes of nitrophenylenediamines, nitroaminophenols and aminoanthraquinones.

Semi-permanent hair dyes are particularly important because they provide a range of hair shades impossible to obtain with the oxidation dyes employed in permanent hair colorings.

Permanent hair colorings are those that are resistant to shampooing, brushing, friction, light, etc. The oxidation dyes, or para-dyes, used in permanent hair coloring are colorless until oxidized by an oxidizing agent, typically hydrogen peroxide or a derivative.

In addition to acting as an oxidizing agent, hydrogen peroxide is also important in its ability to solubilize the natural melanin pigments of the hair, consequently bleaching or lightening the hair. Thus, hair can be lightened, for example, to provide a blonde shade by employing hydrogen peroxide to first remove natural pigments, and then to impart a new color to the lightened hair with oxidation dyes. Typically, a combined bleach and oxidation dye will be employed to bleach the hair while the dyes are penetrating. This method allows dark hair to be lightened by several shades while giving the appearance of not having been bleached.

Hydrogen peroxide has also been employed in combination with a 1:2 chromium complex of a mono azo dye and in combination with a dye derived from triarylmethane to lighten and tint hair. These types of dyes are generally classed as temporary hair dyes as discussed above.

Although the above methods are adequate to provide effective hair coloring, they have several disadvantages. Only the permanent oxidation dyes will provide lasting results. However, even so-called permanent oxidation dyes will leach out over a relatively short period of time, e.g., over a period of one to twelve weeks depending on the number of shampooings, the condition of the hair, etc. Color setting lotions, for example, the 1:2 chromium complex of a a mono azo dye discussed above, must generally be applied weekly to maintain the desired color. For more permanent colors, the length of time between treatments is upwards to a month. However, when hydrogen peroxide is employed, especially in color setting lotions employed to lighten and impart shading to hair at the same time, the frequent application of hydrogen peroxide can severely damage the hair. In the case of oxidation dyes, unwanted tones resulting from the treatment cannot be corrected without adding additional harmful hydrogen peroxide, which undesirably further lightens the hair.

Additionally, there is an added risk in using oxidation dyes due to skin irritation or sensitization and systemic toxicity. For example, the common oxidation dye components p-phenylenediamine and p-toluylenediamine, are capable of causing contact dermatitis.

Aside from the temporary results, complications and risks of the traditional hair dying techniques mentioned above, hair colorists have strived to improve their ability to add color and shades to hair. One desire is to duplicate as closely as possible the color and shadings, or highlights, achieved by the action of sunlight on the hair. Heretofore, a method of achieving effects much like the natural effects of sunlight through a hair coloring process that not only attained the desired results, but avoided the temporary nature of many techniques, or the excessive and prolonged use of hydrogen peroxide and potentially harmful oxidation dyes, has not been known.

SUMMARY OF THE INVENTION process of
The present invention is a novel process of lightening the natural color of hair and imparting desired complementary shades without the use of oxidation dyes. Additionally, the results achieved are more permanent or longer lasting than those obtainable by the use of oxidation dyes. Moreover, the invention provides a novel technique for achieving coloring effects similar to the action of the sun by allowing the natural hair color to be lightened while permanently imparting the shades and highlights which complement or neutralize the natural hair color.

Accordingly, the present invention achieves these results by applying a sufficient amount of a hair bleaching agent to hair for a sufficient length of time to obtain a lightened natural hair color to a predetemined degree. A portion of the hair which is contacted by the hair bleaching agent is further contacted with a sufficient amount of a non-oxidation type colorant capable of penetrating the hair bleaching agent and imparting a permanent shade to the lightened hair. The hair bleaching agent and the colorant are left in contact with the hair until the desired effect is obtained, and then rinsed.

To achieve the natural effects of sunlight, colors of red, yellow, blue, orange, violet, green, white, black and the like, can be applied to the hair in a stripe-like or layered fashion. Once the hair bleaching agent and colorant have remained in contact with the hair long enough to achieve the desired result, the hair is rinsed, leaving a hair with an overall lightened color, but having various shades and highlights which complement the lightened natural hair color, much like the natural effects of sunlight. The results are a multitude of shades derived by the simultaneous application of a multitude of colors rather than a homogeneous shade which is derived by the traditional application of oxidation type dyes.

Unlike traditional oxidation dyes, a permanent color is imparted to the hair while exposing the hair to harmful hydrogen peroxide for less time. Surprisingly, permanents are not affected by the hair lightening and coloring of the present invention as they are by traditional oxidation dye treatments. Additionally, once the treatment is completed, e.g., after rinsing and drying, unwanted tones can be permanently corrected by directly applying colorant to the desired parts of the hair without the use of additional hydrogen peroxide.

DETAILED DESCRIPTION AND PREFERRED EMBODIMENT

The present invention employs a hair bleaching agent to achieve a lighter hair color, and contacting at least a portion of the hair so contacted with the hair bleaching agent with a non-oxidation type colorant which surprisingly imparts a permanent shading to the hair.

Hair Bleaching Agent

Pigment granules in the cells of the hair shaft cause the natural color of hair. There are basically two types of pigments, or melanin, in hair. These are eumelanin, which is brown or black, and phaeomelanin, which is yellow or reddish. While these two pigments determine hair color, or shade, the size of the individual melanin granules determines how dark the hair color will be; larger granules causing darker hair color.

It is known that bleaching agents act on part of the melanin in the hair to oxidize it, thus solubilizing a portion of the melanin in the hair and consequently lightening the natural hair color. A bleaching agent as used here means any agent capable of acting to physically or chemically remove the color causing compounds contained in the hair to cause the hair color to become lighter, including but not limited to hydrogen peroxide, an admixture of hydrogen peroxide and hair bleaching powder, or any other commercially available hair bleach.

In the subject invention, hydrogen peroxide is employed as the main hair lightening constituent. Although hydrogen peroxide can be employed by itself in lightening hair color, in the preferred embodiment of the present invention, the hydrogen peroxide is combined with commercially available hair bleaching powder. The hair bleaching powder allows the hydrogen peroxide to be applied to the hair in a more controlled manner. For example, hair bleaching powder is mixed with hydrogen peroxide in varying ratios to achieve a paste having varying strengths of hydrogen peroxide, consequently providing varying bleaching or hair lightening rates. If desired, a conditioning agent can be ,incorporated into the mixture, for example milk, beer or olive oil, to help counteract the damaging effects of hydrogen peroxide.

Colorant

Any type of pigment type coloring agent can be employed in the practice of the present invention, either organic or inorganic, including but not limited to pigments such as, raw sienna, burnt sienna, red sienna, ultramarine blue, yellow, brown or red ocher, cobalt blue, umber, and organic pigments, either synthetic or natural, such as the pigments contained in the groups chlorophylls, carotenoids, and flavanoids.

Especially effective as permanent hair colorants as used in the present invention are tempera paints, e.g., watercolor paints consisting of pigment ground in water and mixed with egg yolk. These are the paints typically used as finger paints. An especially effective tempera paint for use as a permanent hair colorant as used in the present invention are acrylic type tempera paints, typically used by artists in silk-screening. Permanent as used in the present invention means more permanent or longer lasting than the results obtainable by so-called permanent oxidation dyes.

Tempera paints, generally, are emulsions comprising pigments ground in a medium miscible with water. The emulsions-comprise an oily ingredient such as oil, wax or resin, and an aqueous, thick gummy or glue-like ingredient.

The following examples are to further illustrate the invention in detail, and in no way are meant to limit the scope of the invention.

EXAMPLE 1

Illustration of Typical Application

A plastic bag is placed over the hair to be treated to minimize contact between the scalp and a bleaching agent. A perforation is made in the plastic bag in the vicinity of the hair desired to be treated, and that portion of the hair is pulled through the holes, for example, by a crochet needle. Other perforations are made, and other hair is pulled through until all the hair desired to be treated is outside the plastic bag. Less hair is pulled through if only shadows are desired, and more is pulled through for a brighter effect. In the alternative a pre-perforated plastic bag may be used with the hair pulled through the perforations in a similar manner.

The hair bleaching agent and the colorant can be applied either as one mixture, i.e., the colorant mixed with the hair bleaching agent, or in succession, one after the other, i.e., the hair bleaching agent, then the colorant applied on top. In any event, sufficient colorant must be employed so as to contact the hair through the bleaching agent.

It is desirable to apply the colorant, whether alone or in combination with the bleaching agent, with an artist's brush or artist's air brush. Application on subjects with short hair is started on strands of hair beginning at the nape of the neck, using a comb to separate the strands of hair. Application on subjects with long hair can be accomplished in a similar manner or in stripes which are at right angles to the shaft of the hair with the hair combed straight back from the forehead to the back of the subject. The stripes of colorant begin at the forehead and progress to the subject's back.

To achieve the desired effect, various colors can be applied, preferably in successive bands, to the same strand of hair. For example, a ½ inch band of blue and white can be applied to the tip of the hair, followed by a ½ inch band of violet, a ½ inch band of yellow, a ½ inch band of green, and an inch of deep blue. The application of colors and the mixture of the various colors varies from application to application depending on the color and condition of the hair before the tinting begins and the final result desired.

Preferably the application step is repeated on other strands of hair, working from the nape of the neck up, until all the hair strands desired to be treated with the desired color combinations have been completed.

The bleaching agent and the pigment is left on the hair until the desired lightness of hair is achieved. If desired, a plastic bag can be placed over the top of the head, and heat applied to speed the hair lightening and tinting process.

After treatment, the perforated plastic bag is left on the head and the treated strands are rinsed. The bag is then removed, and the hair is washed, rinsed, etc.

In yet another novel and surprising feature of the present invention, unwanted tones, colors, shades, etc. can be corrected after the treatment, in a permanent fashion, by simply applying a desired colorant alone to the treated strands of hair, rather than applying oxidation dyes and additional harmful hydrogen peroxide as with the conventional method. Moreover, since no hydrogen peroxide is employed in correcting unwanted colors, the hair is not further lightened. Further, additional pigment can be applied to all the hair, since only the hydrogen peroxide treated hair will be affected. In a similar fashion, various colors can be applied to different parts of the hair to accentuate the tones in various areas while at the same time maintaining a multitude of tones throughout the hair.

EXAMPLE 2

Hair bleaching agent was prepared as follows: 1 scoop (approximately ½ ounce or about 14.5 grams) of hair bleaching powder (Framesi decolor B) was mixed with 50 ml of 6% hydrogen peroxide (Framesi-Ossidorr). Distilled water was added until a desired consistency was achieved.

EXAMPLE 3

Several non-toxic liquid acrylic tempera paints (Chromacryl Tempera Paint) for use with the hair bleaching powder of Example 2 was prepared by combining 50 ml of tempera paint with 5 ml of olive oil used as a conditioning agent.

EXAMPLE 4

(a) Virgin, unbleached hair of a medium brown color having a normal texture was painted with a colorant prepared according to Example 3. No bleaching agent was employed. Separate swatches of the medium brown hair were painted with blue, yellow, red, and green. The colorant component was left on the hair for 30 minutes, then rinsed and dried. No visible change to the original medium brown hair color was observed.

(b) Virgin, unbleached hair of a golden blond color having a normal texture was painted with a blue tempera prepared according to Example 3. The colorant was left on the hair for 30 minutes then rinsed and dried. No visible change to the original golden blond color was observed.

EXAMPLE 5

(a) Bleaching agent prepared according to Example 2 was applied to unbleached hair of a medium brown color at a room temperature of 72° F. The bleaching agent was left on the hair for 30 minutes. The hair was rinsed and dried. An orangy blond color was observed. Separate swatches of the orangy blond hair were painted with colors prepared according to Example 3. The colors were left on the hair for 15 minutes, then rinsed and dried. The results are indicated in Table 1.

TABLE 1

| Color Painted | Final Color Observed |
| --- | --- |
| Yellow | Yellow gold blond |
| Blue | Light gold (not as bright) |
| Green | Cooler yellow (still shiny) |
| Violet | Much less gold (more red) |
| Red | Bright reddish blond |

(b) Bleaching agent prepared according to Example 2 was applied to unbleached hair of a gold bond color at a room temperature of 72° F. The bleaching agent was left on the hair for 30 minutes, then rinsed and dried. A very pale blond color was observed. Separate watches of the hair were painted with colors prepared according to Example 3. The colors used and the results observed are indicated in Table 2.

TABLE 2

| Color Painted | Final Color Observed |
| --- | --- |
| Yellow | Very light yellow blond |
| Blue | Silvery blond |
| Green | Light cool ash blond |
| Violet | Violety beige (not shiny but shadowed) |
| Red | Light bright reddish blond (shiny) |

EXAMPLE 6

Unbleached hair of a medium brown color having normal texture was lightened using a mixture prepared according to Example 2. The bleaching agent was left on the hair for 15 minutes, then rinsed and dried. A reddish, golden brown was observed. Swatches of the hair were painted with colors prepared according to Example 3. The colors used and the results observed are indicated in Table 3.

TABLE 3

| Color Painted | Final Color Observed |
| --- | --- |
| Blue | Less orangy (but not as bright) |
| Yellow | More gold (less red) |
| Green | Less bright, less red |
| Red | Brighter, more red |

EXAMPLE 7

Bleaching agent prepared according to Example 2 and colorant prepared according to Example 3 were combined and painted on swatches of unbleached hair of (a) medium brown color, and (b) gold blond color. The combined mixture was left on the medium brown color hair for 30 minutes, and on the gold blond hair for 15 minutes. The colors used and the results observed are indicated in Table 4.

TABLE 4

| Color Painted | Final Color Observed (Medium Brown Hair) (30 min. application time) | Final Color Observed (Blond Hair) (15 min. application time) |
| --- | --- | --- |
| Green | Light gold blond, less red | Very light cool blond |

TABLE 4-continued

| Color Painted | Final Color Observed (Medium Brown Hair) (30 min. application time) | Final Color Observed (Blond Hair) (15 min. application time) |
|---|---|---|
| Yellow | More gold, less red | Very light, bright yellow blond |
| Blue | Less gold, less, red, less brown | Silvery blond |
| Red | Light, bright reddish blond | Shiny, very light reddish blond |
| Violet | Light blond, somewhat beige | Very light beige blond |

EXAMPLE 8

Hair bleaching agent prepared according to Example 2 and colorant prepared according to Example 3 were applied to dark blond and left on the hair for 15 minutes. Thereafter, the hair was rinsed, dried, shampooed and set. Over the course of several weeks the hair was washing in excess of thirty times, brushed, combed and exposed to sunlight. No visible change in the color of the treated hair was observed.

What is claimed is:

1. A method of lightening and shading a human head of hair containing natural hair colorants comprising the following steps:
   (a) applying hair bleaching agent to at least a portion of the hair in a quantity and for a time sufficient to lighten the natural color of the hair;
   (b) during or following step (a), applying separate pigment colorants to different portions of the hair to which the bleaching agent was applied in step (a) in amounts for times sufficient to impart shading to the hair, wherein the pigment colorants are rinsable off the hair and the pigments colorants applied to adjacent portions of the hair have different shades; and
   (c) rinsing said bleaching agent and said pigment colorants off the hair while natural colorants remain in the hair.

2. The method of claim 1 wherein said bleaching agent comprises hydrogen peroxide.

3. The method of claim 2 wherein said bleaching agent further comprises hair bleaching powder.

4. The method of claim 1 wherein the pigment colorants comprise tempera paints.

5. The method of claim 1 wherein the bleaching agent and pigment colorants are applied as different stripes extending between the forehead and the back.

6. The method of claim 1 wherein the bleaching agent and pigment colorants are applied to different layers of the hair.

7. The method of claim 1 wherein the bleaching agent and pigment colorants are applied to successive bands along strands of the hair.

8. A method of lightening and shading a human head of hair containing natural hair colorants, comprising:
   (a) applying a hair bleaching agent to at least a portion of the hair in a quantity sufficient to lighten the natural color of the hair;
   (b) applying different pigment colorants separately to different portions of the hair being lightened in quantities sufficient to contact such portions and impart shading to such portions, said pigment colorants being of types rinsable off the hair;
   (c) leaving the hair bleaching agent and the pigment colorants so applied to the hair in contact with the hair sufficiently to lighten and shade the hair; and
   (d) rinsing the bleaching agent and the pigment colorants off the hair following such lightening and shading.

9. The method of claim 8 in which the pigment colorants are applied following the application of the bleaching agent.

10. The method of claim 8 in which the pigment colorants are applied during the application of the bleaching agent.

11. The method of claim 8 in which at least some of the pigment colorants are tempera paints.

12. The method of claim 11 in which the tempera paints are acrylic tempera paints.

13. The method of claim 8 in which the pigment colorants comprise pigments ground in a medium miscible with water.

14. The method of claim 13 in which the pigment colorants are applied in a manner to form stripes of different colors extending between the forehead and the back of the head.

15. The method of claim 13 in which the pigment colorants are applied in a manner to form hair layers of different colors.

16. A method of lightening and shading a human head of hair containing natural hair colorants, comprising the following steps:
   (a) applying hair bleaching agent to at least a portion of the hair in a quantity sufficient to lighten the natural color of the hair;
   (b) leaving the bleaching agent so applied on the hair for a time or times sufficient to lighten the hair;
   (c) rinsing the bleaching agent off the lightened hair;
   (d) applying to the rinsed hair, including the lightened portion, a plurality of separate pigment colorants, such pigment colorants being in a form rinsable off the hair and applied in a manner and in sufficient quantities to contact and impart different shades to different portions of the hair;
   (e) leaving the pigment colorants so applied on the hair for a time or times sufficient to impart shades to the lightened portions of the hair; and
   (f) rinsing said pigment colorants off the hair.

17. A method of lightening and shading a human head of hair possessing its natural melanin color which comprises the following steps:
   (a) applying hair bleaching agent to at least a portion of the head of hair in an amount and for a time sufficient to lighten the color of the hair;
   (b) during or following Step (a) contacting different parts of the hair to which the bleaching agent has been applied with a multitude of separate, water rinsable pigment colorants, such that adjacent said parts are contacted by different such pigment colorants in quantities and for a time or times sufficient to impart a multitude of shades to the hair; and
   (c) rinsing said bleaching agent from the hair following Step (a) or Step (b) and rinsing said pigment colorants from the hair following Step (b).

18. The method of claim 17 which further comprises covering the head of hair prior to Step (a) with a cap having multiple spaced perforations, pulling different portions of the hair through such perforations; and thereafter treating the pulled portions according to Steps (a) through (c).

19. The method of claim 17 in which the different parts comprise strands of hair.

20. The method of claim 17 in which the different parts comprise different bands of hair.

21. A method lightening and shading a human head of hair possessing its natural melanin color which comprises the following steps:
 (a) applying hair bleaching agent to at least a portion of the head of hair in an amount and for a time sufficient to lighten the color of the hair;
 (b) during a following step (a) contacting different parts of the hair to which the bleaching agent has been applied with a multitude of separate, water-rinsable pigment colorants, such that adjacent said parts are contacted by different such pigment colorants in quantities and for a time or time sufficient to impart a multitude of shades to the hair;
 (c) following step (b) applying heat to at least those portions of the hair contacted by the bleaching agent and the pigment colorants; and
 (d) following step (c) rinsing said bleaching agent and said pigment colorants from the hair.

* * * * *

UNITED STATES PATENT AND TRADEMARK OFFICE
CERTIFICATE OF CORRECTION

PATENT NO. : 5,224,964
DATED : July 6, 1993
INVENTOR(S) : Farouk M. Shami

It is certified that error appears in the above-indentified patent and that said Letters Patent is hereby corrected as shown below:

Column 2, line 41, delete "process of".

Column 3, line 67, delete "pigment", and insert -- non-oxidation --.

Column 4, line 21, delete "emulsions-comprise", and insert -- emulsions comprise --.

Column 7, line 36, delete "amounts for", and insert -- amounts and for --.

Column 8, line 43, delete "colorants", and insert -- colorant --.

Column 8, line 68, delete "through", and insert -- and --.

Signed and Sealed this

Fifteenth Day of March, 1994

BRUCE LEHMAN

Attest:

Attesting Officer

Commissioner of Patents and Trademarks